United States Patent
Woodcock et al.

(10) Patent No.: US 7,761,302 B2
(45) Date of Patent: Jul. 20, 2010

(54) METHOD FOR GENERATING OUTPUT DATA

(75) Inventors: Ashley Arthur Woodcock, Cheshire (GB); Jaclyn Ann Smith, Manchester (GB); Kevin McGuinness, Cheshire (GB)

(73) Assignee: South Manchester University Hospitals NHS Trust, Manchester (GB)

( * ) Notice: Subject to any disclaimer, the term of this patent is extended or adjusted under 35 U.S.C. 154(b) by 1210 days.

(21) Appl. No.: 11/146,905

(22) Filed: Jun. 7, 2005

(65) Prior Publication Data
US 2006/0277037 A1    Dec. 7, 2006

(30) Foreign Application Priority Data
Jun. 3, 2005    (GB) ................... 0511307.1

(51) Int. Cl.
*G10L 21/00*    (2006.01)
(52) U.S. Cl. .............. 704/270; 704/243; 704/244; 600/538
(58) Field of Classification Search .......... 704/206, 704/207, 209, 243, 244, 231, 236, 245, 250, 704/270, 256; 600/529–542
See application file for complete search history.

(56) References Cited
U.S. PATENT DOCUMENTS

| | | | |
|---|---|---|---|
| 3,593,703 A | 7/1971 | Gunn | |
| 3,821,472 A | 6/1974 | Herscher et al. | |
| 4,668,941 A | 5/1987 | Davenport et al. | |
| 5,170,434 A | 12/1992 | Anderson | |
| 5,928,156 A | 7/1999 | Krumbiegel et al. | |
| 6,241,683 B1 | 6/2001 | Macklem et al. | |
| 6,261,238 B1 * | 7/2001 | Gavriely | 600/532 |
| 6,436,057 B1 | 8/2002 | Goldsmith et al. | |
| 2004/0230432 A1 | 11/2004 | Liu et al. | |

FOREIGN PATENT DOCUMENTS

| | | |
|---|---|---|
| EP | 1603116 A1 | 12/2005 |
| JP | 4-276523 A | 10/1992 |
| WO | WO 2004/091503 | 10/2004 |
| WO | WO 2004/091503 A | 10/2004 |
| WO | WO 2005/002421 A2 | 1/2005 |

* cited by examiner

*Primary Examiner*—Huyen X. Vo
(74) *Attorney, Agent, or Firm*—Krieg DeVault LLP; L. Scott Paynter

(57) ABSTRACT

A method for generating output data identifying a class of a predetermined plurality of classes. The method comprises receiving data representing an acoustic signal; determining an amplitude of at least a first predetermined frequency component of said acoustic signal; and comparing the or each amplitude with a respective primary threshold; and generating output data identifying one of said classes to which said acoustic signal should be allocated, based upon said comparison.

10 Claims, 13 Drawing Sheets

```
                    S4
┌─────────────────────┐
│  DETERMINE VITAL    │
│      CAPACITY       │
└─────────────────────┘
           │
           ▼         S5
┌─────────────────────┐
│ CALCULATE AIR TO BE │
│       EXHALED       │
└─────────────────────┘
           │
           ▼         S6
┌─────────────────────┐
│  CONFIGURE SUBJECT  │
└─────────────────────┘
           │
           ▼         S7
┌─────────────────────┐
│    OBTAIN COUGH     │
│      SAMPLES        │
└─────────────────────┘
```

FIGURE 5

METHOD FOR GENERATING OUTPUT DATA

CROSS-REFERENCE TO RELATED APPLICATIONS

The present application claims priority to British Patent Application No. 0511307.1 filed in the United Kingdom on 3 Jun. 2005.

BACKGROUND OF THE INVENTION

The present invention relates to a method for processing data representing an acoustic signal to generate output data that identifies a class of a predetermined plurality of classes.

Coughing is one of the most common symptoms treated by medical practitioners and is often used to diagnose conditions such as asthma. Coughing is also a condition which is often painful and distressing for sufferers.

An assessment of a cough is typically subjective, being made by a medical practitioner during a consultation. There is no easy way to classify the severity of a cough in such a consultation. Instead, a medical practitioner must use their experience to subjectively assess the severity, and the likely cause of the cough.

One objective indication of the severity of a cough is to count the number of times a patient coughs over a period of time. Such an objective measure can be derived by monitoring a patient over a predetermined time period, and manually recording the number of coughs occurring within that time period. Although such monitoring may provide useful data, it is very labour intensive, requiring constant monitoring. Such monitoring is also intrusive to the patient.

Recently, attempts have been made to automatically and unobtrusively monitor cough events using an appropriately configured electronic device. However, such a device must distinguish cough events from environmental noises, and from speech of the subject. If such a device records a small percentage of speech as a cough, then the device will produce unreliable results, given that the time spent speaking is an order of magnitude greater than the time spent coughing.

PCT patent application publication number WO 2004/091503 discloses a method for processing signals indicative of a monitored subject's respiration, signals representative of the subject's posture and movement and signals representative of the sound made by the subject. The method uses the rib cage size (RC), the abdominal size (AB) of the subject while the subject undertakes different activities. From these measurements, the method determines an estimate of the lung volume (Vt) of the subject. By carrying out various analysis, the described method stated to be able to identify and distinguish between coughs, apnoea, hypopnoea, sighs and dyspnoea.

Although the method and apparatus described in WO 2004/091503 provides useful information, the number of sensors, and particularly the sensors worn to monitor the subject's abdomen and rib cage measurements cause such a device to be extremely uncomfortable. This is particularly undesirable given that a subject may be wearing the device for a substantial period of time.

BRIEF SUMMARY OF THE INVENTION

It is an object of an embodiment of the present invention to obviate or mitigate at least some of the disadvantages set out above.

In this specification the term cough is used to mean an event in which a subject takes a breath in, followed by one or more forced expiratory efforts initially against a closed glottis, accompanied by a characteristic sound.

In accordance with a first aspect of the present invention there is provided a method for generating output data identifying a class of a predetermined plurality of classes, the method comprising:
  receiving data representing an acoustic signal;
  determining an amplitude of at least a first predetermined frequency component of said acoustic signal;
  comparing the or each amplitude with a respective primary threshold; and generating output data identifying one of said classes to which said acoustic signal should be allocated, based upon said comparison.

By considering the amplitude of a frequency component of an acoustic signal, data, which can be used to classify acoustic signals more reliably, can be generated.

In accordance with a second aspect of the present invention there is provided a calibration method for calibrating an apparatus to differentiate acoustic signals attributable to cough from other acoustic signals, the method comprising:
  receiving first data representing a first acoustic signal representing at least one cough;
  receiving first data representing a second acoustic signal representing an acoustic event other than cough; and
  processing said first and second data to generate configuration data for said apparatus, said configuration data defining at least one rule which when applied differentiates acoustic signals attributable to cough from other acoustic signals.

BRIEF DESCRIPTION OF SEVERAL VIEWS OF THE DRAWING(S)

The inventors of the present invention have recognized that by calibrating an apparatus using a cough sample and a non cough sample, a much improved apparatus for differentiating between such acoustic signals can be created.

In accordance with a third aspect of the present invention there is provided a calibration method for calibrating an apparatus to output data identifying a class of a predetermined plurality of classes, each class representing a condition of a human or animal subject, the method comprising:
  receiving data representing a first acoustic signal, said first acoustic signal being obtained at a first predetermined percentage of the subject's vital capacity; and
  calibrating said apparatus based upon said acoustic signal.

The inventors of the present invention have also recognized that to calibrate such an apparatus, the quantity of air within the lungs of the subject is of extreme importance while producing calibration data, if a reliable calibration is to occur.

An embodiment of the present invention will now be described, by way of example only, with reference to the accompanying drawings, in which:

FIG. 5 is a flowchart of calibration carried out in FIG. 1 in further detail;

DETAILED DESCRIPTION OF REPRESENTATIVE INVENTION EMBODIMENTS

Figure 1:
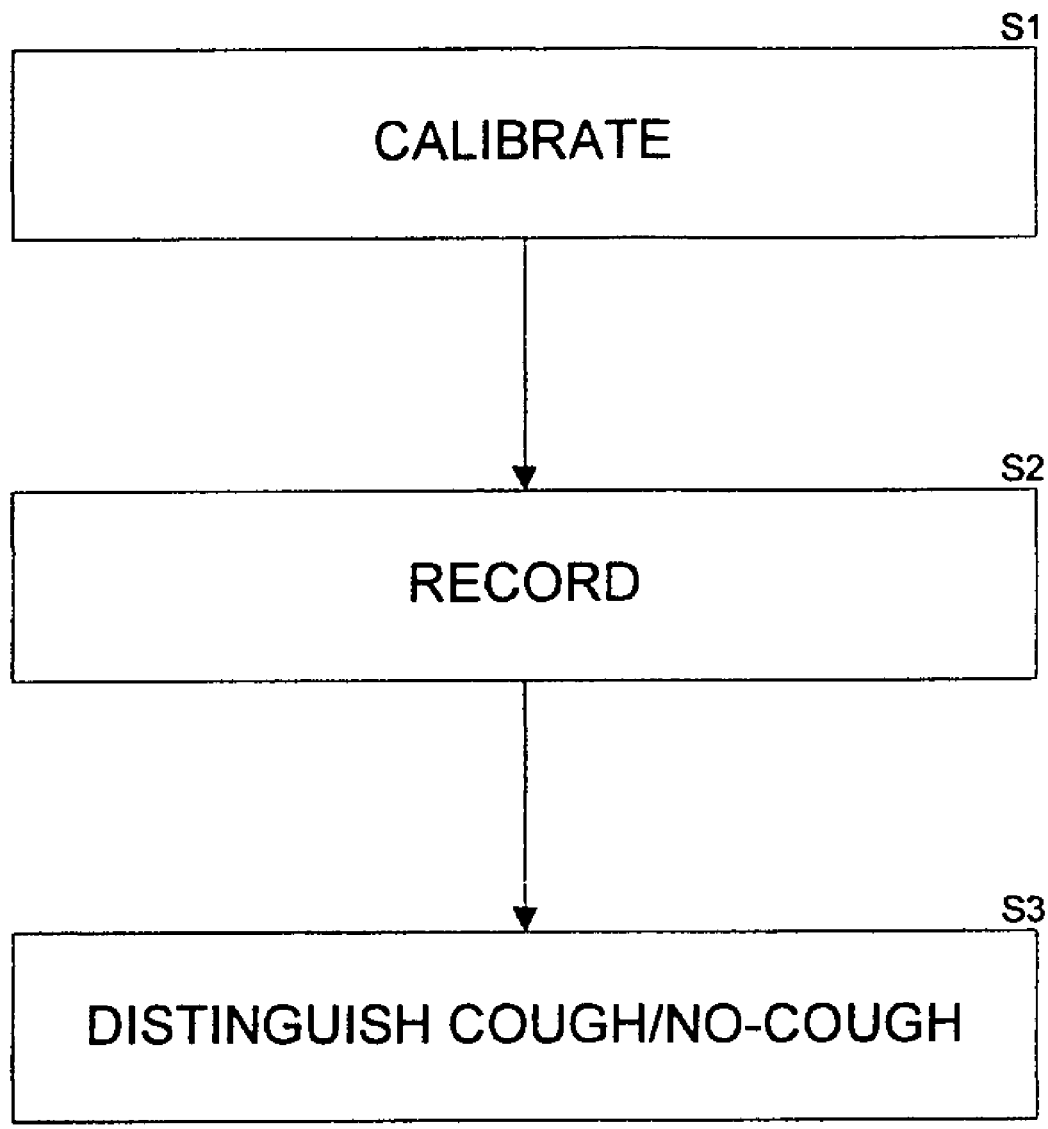
FIG. 1 is a flowchart showing an overview of operation of an embodiment of the present invention.

Referring first to FIG. 1, there is illustrated an overview of processing carried out in an embodiment of the present invention, to distinguish data indicative of a subject coughing from data indicative of other sounds. A first step S1 involves calibration of apparatus, a second step S2 involves recording data representing an acoustic signal, and a third step S3 involves processing data obtained at step S2 to distinguish data indicative of cough from data indicative of other events.

The calibration of step S1, the recording of step S2 and the distinguishing of step S3 all involve processing acoustic signals obtained from a subject. Such acoustic signals are obtained using a sensor positioned on the subject's chest. It will be appreciated that much of the processing of step S3 will distinguish acoustic data attributable to cough from acoustic data attributable to speech. It has been realised that vibrations at the chest wall differ considerably depending on whether the vibrations were caused by cough or by speech, thus sensor placement on the subject's chest allows acoustic signals attributable to cough to be distinguished from those attributable to speech more easily than, for example, using an air-coupled or lapel microphone.

Figure 2:
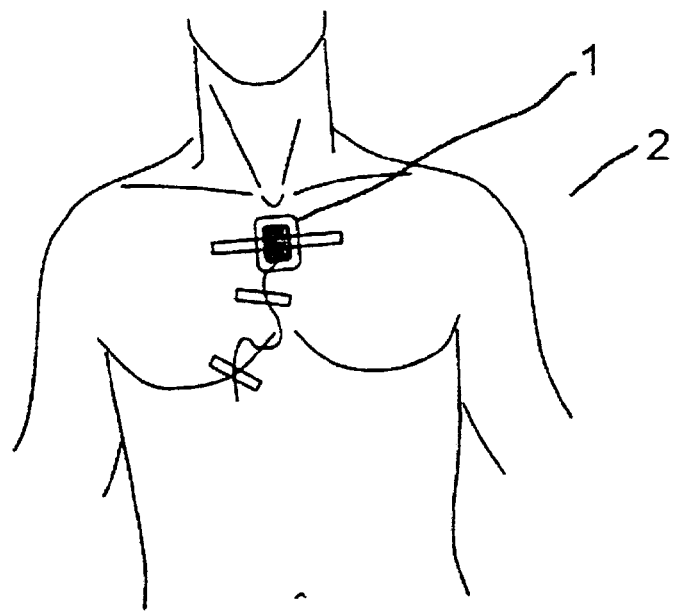
FIG. 2 is a schematic illustration showing sensor placement on a subject's body, for use in the embodiment of FIG. 1.

FIG. 2 illustrates a piezoelectric sensor 1 positioned on a subject's chest 2, the piezoelectric sensor being configured to convert vibrations of the subject's chest wall indicative of an acoustic signal generated by the subject, into an electric signal. It should be noted that the piezoelectric sensor 1 does not detect acoustic signals attributable to other sources. As illustrated in FIG. 2, the piezoelectric sensor 1 is attached to the subject on the manubrium of the subject's sternum, directly below the suprasternal notch. The piezoelectric sensor 1 is positioned as shown in FIG. 2 as it has been found that such positioning keeps the sensor 1 substantially stable, even if the subject moves. Additionally the illustrated position is such as to be the part of the subject's chest where there is least tissue between the skin and the lungs.

Figure 3:
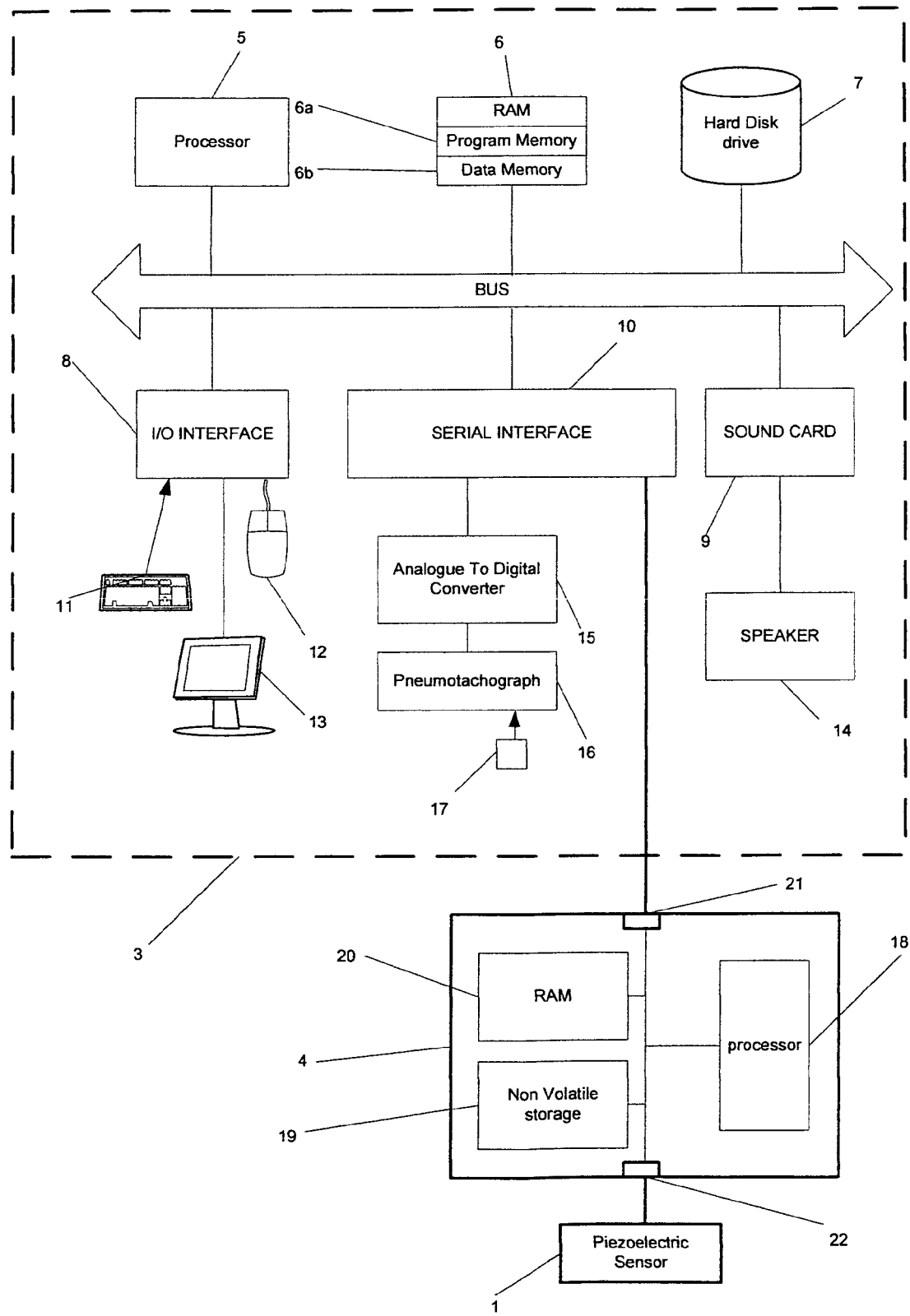
FIG. 3 is a schematic illustration of the architecture of apparatus used in the embodiment of FIG. 1.

Having described the use and positioning of the piezoelectric sensor 1, apparatus used in embodiments of the present invention is now described in further detail with reference to FIG. 3. The illustrated apparatus comprises three main components, the piezoelectric sensor 1 described above, a workstation 3, and a sensor interface 4 configured to receive data from the piezoelectric sensor 1 and provide this data to the workstation 3. It can be seen that the workstation 3 comprises a processor 5 and Random Access Memory (RAM) 6. The RAM 6 is, in use, divided to provide a program memory 6a and a data memory 6b. The processor 5 is configured to execute instructions specified in programs stored in the program memory 6b. The workstation 3 further comprises a non-volatile storage device in the form of a hard disk drive 7. The workstation 3 also comprises an input/output (I/O) interface 8, a sound card 9 and a serial interface 10. The processor 5, the RAM 6, the hard disk drive 7, the I/O interface 8, the sound card 9 and the serial interface 10 are connected together by means of a bus along which both data and instructions are passed.

The I/O interface 8 controls the flow of data between input and output devices and other components of the workstation 3. It can be seen that the I/O interface is connected to a keyboard 11, a mouse 12 and a display screen 13. The sound card 9 is configured to handle output of audio data, and it can be seen that the sound card 9 is connected to a speaker 14 to which audio data is passed. The serial interface 10 allows the workstation 3 to be coupled to various external devices, and it can be seen that the sensor interface 4 mentioned above is connected to the workstation 3 by means of the serial interface 10. The serial interface 10 is further connected to an analogue to digital converter 15 which in turn is connected to a pneumotachograph 16. It will be appreciated that other devices capable of measuring lung volumes can be used.

The pneumotachograph 16 is a conventional piece of apparatus for measuring the amount of air exhaled and inhaled by a subject, and its use is described below. A spirometer could be used in place of a pneumotachograph in some embodiments of the invention. It can be seen from FIG. 3, that the pneumotachograph comprises a mouthpiece 17.

The piezoelectric sensor 1 communicates electrical signals to the workstation 3 via the sensor interface 4. The sensor interface 4 comprises a processor 18, non-volatile storage 19 and RAM 20. The sensor interface 4 further comprises a connector 21 for connection to the workstation 3 and an input 22 for connection to the piezoelectric sensor 1. It should be noted that acoustic signals represented by electrical signals provided by the piezoelectric sensor 1, may be stored in the non-volatile storage 19, thereby allowing the sensor interface 4 to be used as a standalone device for the collection of data, without requiring connection to the workstation 3.

Having described the architecture of apparatus used to implement the present invention, calibration of the apparatus (step S1 of FIG. 1) is now described.

Figure 4:
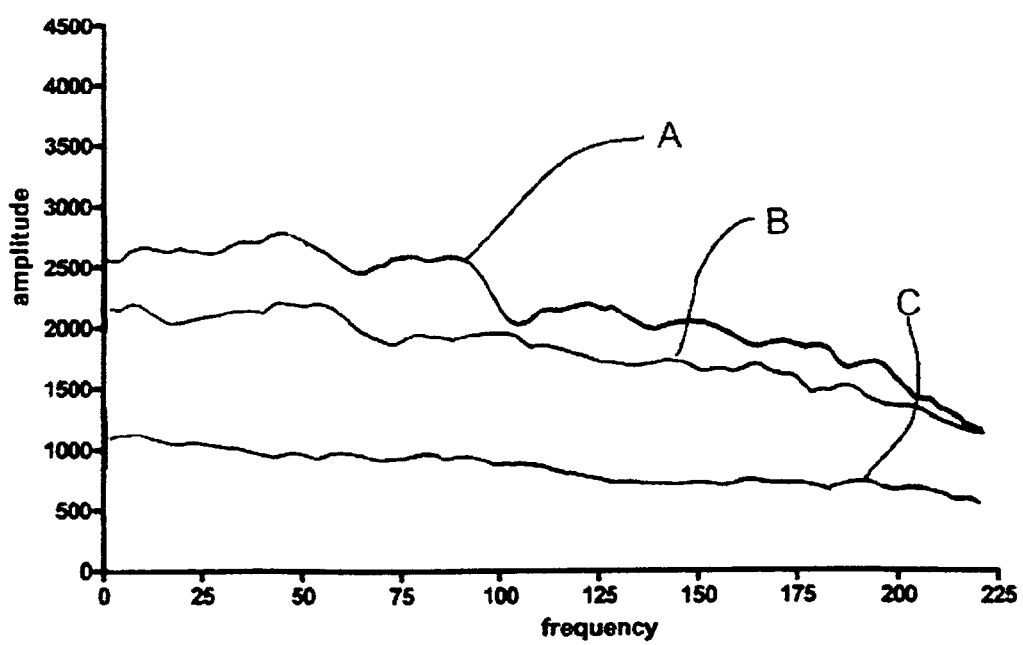
FIG. 4 is a graph showing amplitudes of various frequency components of vibrations caused by coughs, when different quantities of air are present in a subject's lungs.

Experiments have shown that the quantity of air within a subject's lungs when a cough occurs, is a major source of variability in vibrations caused by a cough at the chest wall. Vital capacity is a term used hereinafter to refer to the capacity of a subject's lungs, and FIG. 4 shows plots of the amplitudes of vibrations of various frequencies, caused by coughs produced by a subject when the quantity of air in the subject's lungs was 90%, 60% and 30% of their vital capacities (lines A, B, C respectively). It can be seen from FIG. 4 that, the greater the quantity of air within a subject's lungs (expressed as a fraction of vital capacity) the greater the amplitudes of the generated vibrations.

It should be noted that the amplitudes of vibrations of the chest wall caused by speech are typically small as compared with vibrations caused by cough. Thus, by carrying out calibration to differentiate between data obtained using the piezoelectric sensor 1 in response to a subject coughing with a relatively small quantity of air in their lungs, and data obtained using the piezoelectric sensor 1 in response to the subject speaking, the device is able to effectively differentiate between data indicative of a subject coughing and data indicative of a subject speaking.

Calibration is now described with reference to FIG. 5, which shows the processing of step S1 of FIG. 1 in further detail. As described above, the quantity of air within a subject's lungs when calibration measurements are obtained is an important factor in the calibration process. This quantity is measured as a fraction of a subject's vital capacity, which is determined at step S4 of FIG. 5. Having determined vital capacity at step S4, the quantity of air to be exhaled (following a maximum inspiration) when calibration readings are taken, is determined at step S5. At step S6, arrangements are made so as to ensure that the subject has the desired quantity of air within his/her lungs (described in further detail below). Having ensured that the necessary quantity of air is present within the subject's lungs at step S6, acoustic signals indicative of cough events are obtained at step S7 using the piezoelectric sensor 1.

Figure 6:
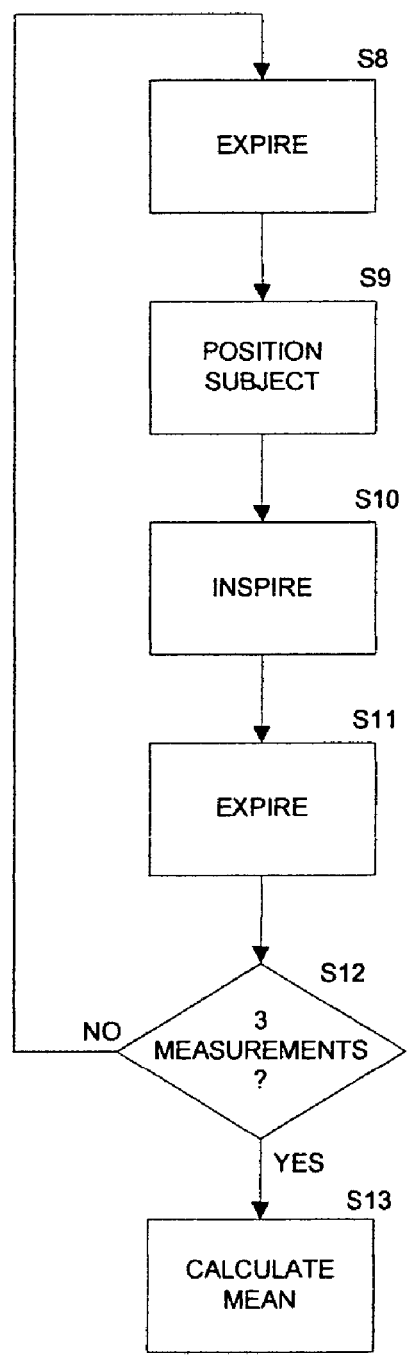
FIG. 6 is a flowchart of a process for determination of a subject's vital capacity.
Figure 7:
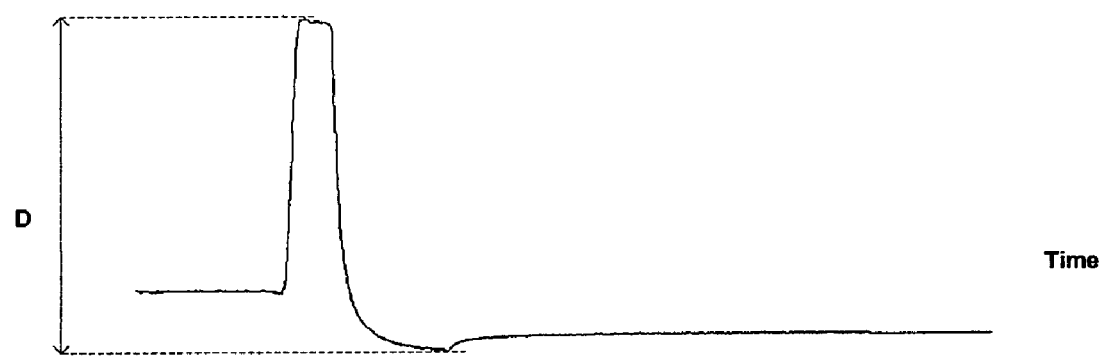
FIG. 7 is a graph representing air movement against time in the process of FIG. 6.

FIG. 6 shows determination of vital capacity (carried out at step S4 of FIG. 5) in further detail. At step S8 the subject 2 breathes out fully (a maximum expiration). At step S9, the subject is positioned such that their lips are sealed around the mouthpiece 17 of the pneumotachograph 16. Having positioned the subject in this way, the subject takes a full breath in (a maximum inspiration) at step S10, and then makes a second maximum expiration at step S11. The pneumotachograph outputs volume data which is displayed on the monitor 13 in the form of a graph as illustrated in FIG. 7. The subject's vital capacity is denoted D on the graph of FIG. 7. The value obtained for the vital capacity is stored in the data memory 6b of the workstation 3.

Referring back to FIG. 6, step S12 ensures that steps S8 to S11 are repeated three times so as to obtain three measurements of vital capacity. Having obtained three measurements of vital capacity, the mean average of these three measurements is calculated at step S13. This average value is, for the purposes of subsequent processing, used as the vital capacity of the subject 2.

As explained above with reference to FIG. 4, coughs with vibrations which most resemble the vibrations of speech are produced by a subject coughing with a small amount of air in his/her lungs. However, it has also been found that there is a need for a minimum quantity of air within a subject's lungs to make coughing physically possible. It is therefore currently preferred that calibration cough samples are obtained when the subject has a quantity of air that is 25%-40% of their vital capacity in their lungs. More preferably the subject has a quantity of air that is 25% to 35% of their vital capacity within their lungs, and most preferably air to 30% of the subject's vital capacity is within their lungs.

Figure 8:
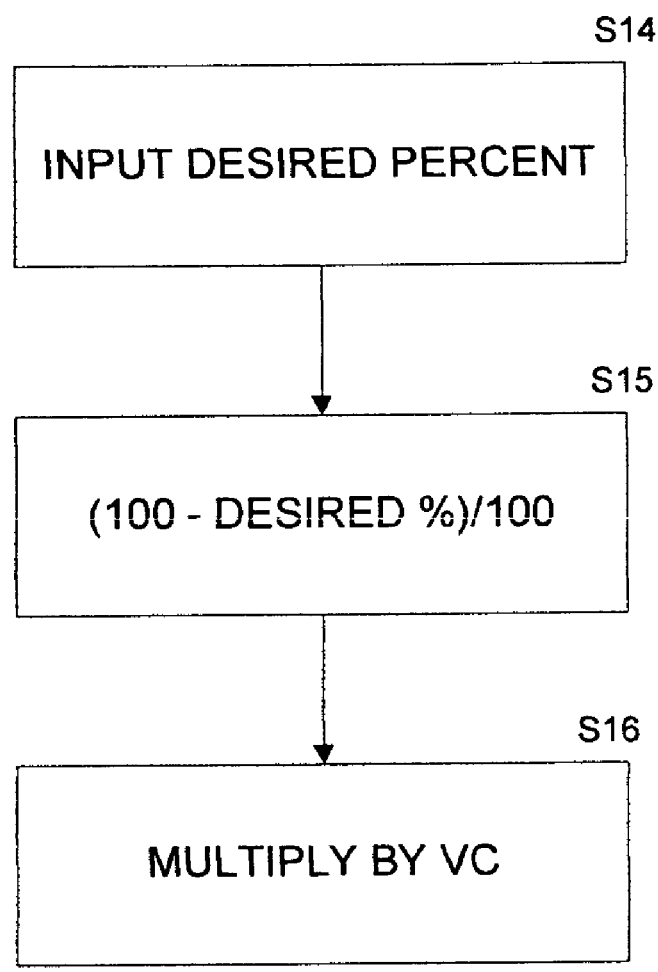
FIG. 8 is a flowchart showing a process for determining the quantity of air to be present within a subject's lungs, in the process of FIG. 1.

FIG. 8 shows processing carried out at step S5 of FIG. 5 in further detail. The desired percentage of the vital capacity is input to the workstation 3 by means of the keyboard 11 at step S14. The input value is subtracted from 100 at step S15, and the resulting value is then divided by 100 and the result multiplied by the vital capacity as determined at step S4 of FIG. 5. Such a process can be pre-programmed into the program memory 6a. This calculation generates a value which can be used to configure the subject, prior to obtaining acoustic signals indicative of cough, as described below.

To obtain an acoustic signal indicative of a cough, the subject 2 is asked to make a maximum expiration, before sealing their lips around a mouthpiece 17 of the pneumotachograph 16. The subject then makes a maximum inspiration and breathes the calculated amount of air into the mouthpiece 17 of the pneumotachograph 16. Given the calculation illustrated in FIG. 8, this will mean that the quantity of air within the subject's lungs is the percentage of the subject's vital capacity input at step S14. The subject 2 then removes their lips from mouthpiece 17 and coughs.

Figure 9:
FIG. 9 is an illustration of a visual indicator showing an extent to which a subject should breathe out.

To enable the subject to become aware that they have exhaled the previously calculated amount of air, the processor 5 of the workstation 3 is programmed to provide an audible and/or visible indication, via the monitor 8 and/or the speaker 10. For example, the quantity of air and the rate at which the subject inhaled and exhaled during such a process may be displayed to the subject in the form of a graph illustrated in FIG. 9a. The visible indication in the present embodiment takes the form of a straight line across a display on the monitor denoted E. An audible indication may take the form of a high pitched sound emitted by the speaker 10, produced when the subject has exhaled sufficiently.

Figure 10:
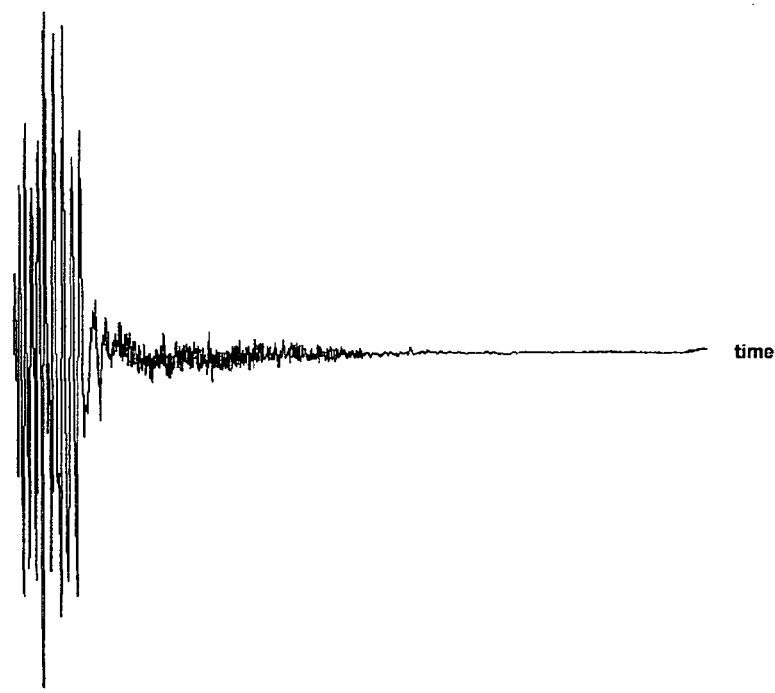
FIG. 10 is a graph representing the amplitude of vibrations caused by a cough against time.

Referring back to FIG. 5, steps S6 and S7 are repeated 20 times, producing 20 coughs at, preferably, 30% of the vital capacity of the subject 2. Data representative of the acoustic signals caused by the 20 coughs is recorded via the piezoelectric sensor 1, the recordings being stored on the hard disk drive 7 in the form of 20 data files. A plot of the amplitude of the vibrations against time caused by a typical cough is shown in FIG. 10.

In order to calibrate the apparatus used to implement the invention, it is necessary to obtain samples of the subject speaking, so as to allow the apparatus to effectively differentiate between acoustic signals attributable to cough, and acoustic signals attributable to speech. Appropriate speech samples are therefore obtained. Two sets of samples are preferably obtained, the first sample being a recording of the subject reading a specially selected passage and the second set of samples being a recording of the subject having a conventional conversation. The specially selected passage preferably contains all the phonetic sounds of the subject's native language. For a native English speaking subject, a passage known as the "The Rainbow Passage" (Fairbanks G: "Voice and Articulation Drillbook", $2^{nd}$ ed., New York, Harper, 1960, pages 124-139) can be used. Alternately, the passage may just contain the phonetic sounds of a language that most resemble coughing when recorded by the piezoelectric sensor 1.

Figure 11:
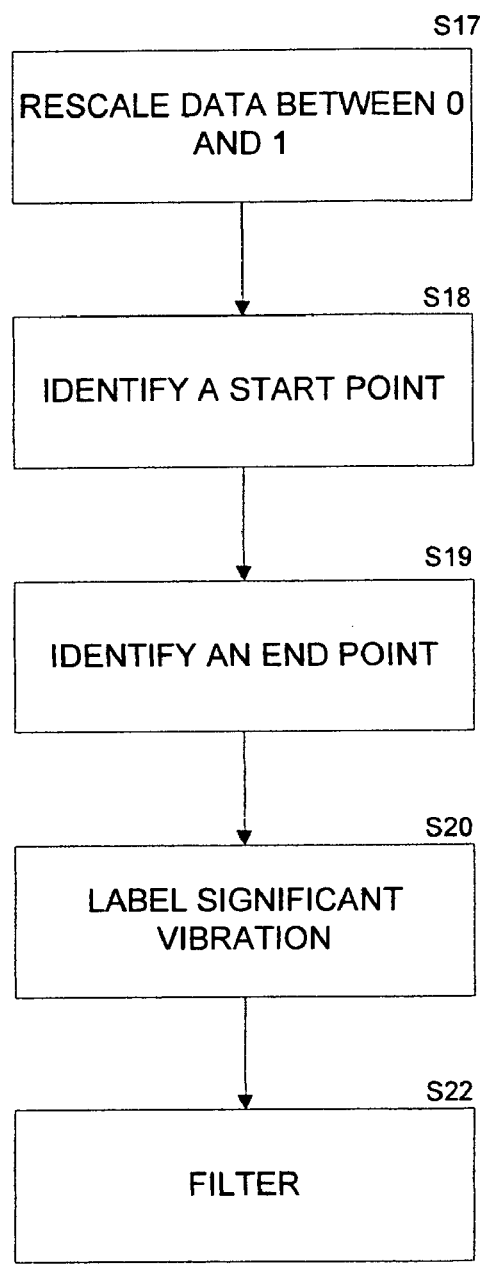
FIG. 11 is a flow chart of a filtration process used to remove data which is not relevant to cough determination.

FIG. 11 illustrates processing carried out on the obtained cough recordings, which are preferably sampled at a frequency is of 8000 Hz. The positions of individual sound events in the continuous cough and non-cough calibration data need to be identified. The speech and cough data is normalised. The start of a significant sound event is identified when a sample point is greater than a preset level. The point at which 400 consecutive point remain below a preset level indicates the end of the sound event. The positions of each event in the cough and speech calibration data are thus determined and recorded.

Analysis of the cough file will produce 20 cough sounds. The number of sound events produced by the speech calibration will be variable, depending upon the length of conversational speech and the speech manner.

Having processed each of the calibration files, each of the significant vibrations is then each filtered by a plurality of Butterworth high pass filters (step S22). Each of these filters will apply a different threshold, in the range 1.8 kHz to 4 kHz at intervals of 10 Hz. The maximum amplitude within the filtered data after application of each filter is recorded. Given that 221 filters are applied, this generates a 221 point curve, each point being associated with the threshold frequency of the filter responsible for its creation. Thus, a frequency domain wave form is created. This approach has the potential for allowing real-time filtering of the source signal, and direct determination of true trigger level for cough identification in an analogue based device. Alternatively, digital sampling and standard signal processing techniques (such as Fourier Transforms) could be applied to the time domain waveform to generate the frequency domain waveform.

The processing represented by steps S17 to S22 of FIG. 11 is repeated for each of the cough files in turn, and is also repeated for each of the speech files in turn. Thus, having repeated the processing of FIG. 11 for each file, a frequency domain waveform for each obtained acoustic signal is available. The next stage of processing involves the removal of obtained sounds which are unlikely to contribute useful information to the calibration process. Such processing is carried out separately for cough samples and speech samples. The processing carried out for each type of sample is shown in FIG. 11.

Figure 12:
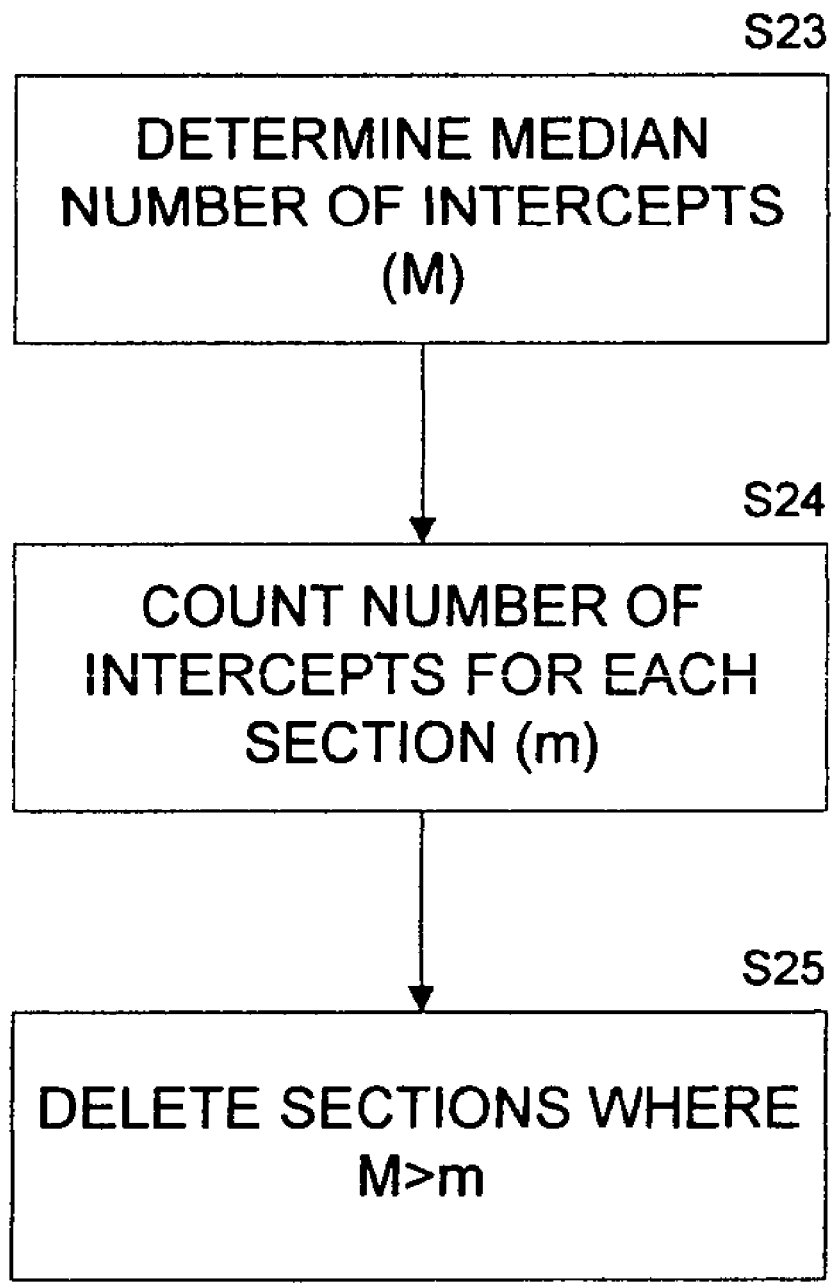
FIG. 12 is a flowchart of a process used to remove outlying signals.

Referring to FIG. 12, at step S23, the number of intercepts with other curves (in the frequency domain) for each curve is determined, and the median of these numbers is also determined. This generates respective median values for cough samples, $M_{Cough}$ and speech samples. $M_{Speech}$.

Having generated these median values, the number of intercepts for each curve is counted, $m_i$ (step S24). If a curve has a lower number of intercepts than the respective median number, then it is discarded (step S25).

Figure 13A:
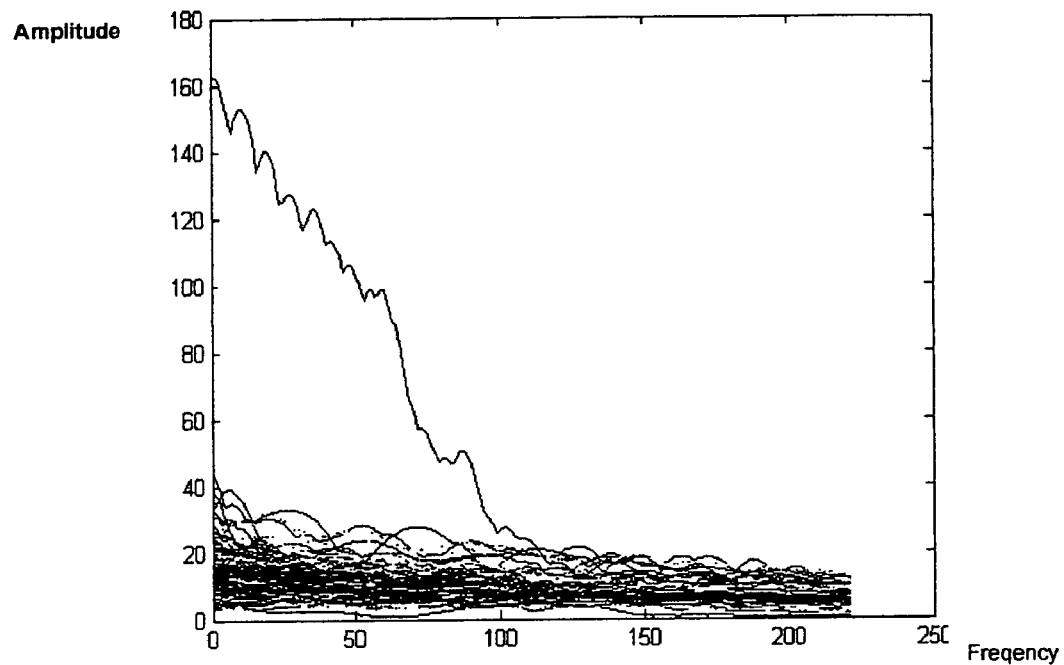
FIGS. 13a and 13b are graphs showing the effect of removing outlying signals from obtained data.
Figure 13B:
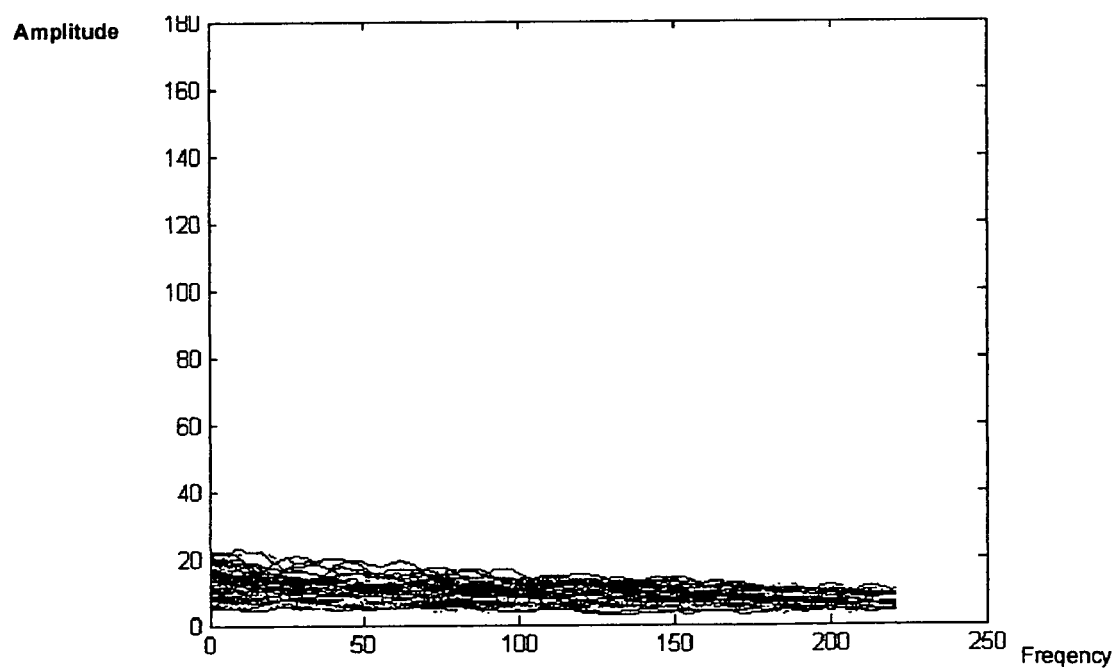

FIGS. 13a and 13b show the effect of removing outliers from a typical set of speech samples. FIG. 13a illustrates frequency domain waveforms for each obtained speech sample, and it can be seen that one of the waveforms is clearly very different from all of the others, while others of the waveforms are considerably different to most of the others. FIG. 13b shows the waveforms obtained when outlying waveforms are removed in the manner described above with reference to FIG. 12.

Figure 14:
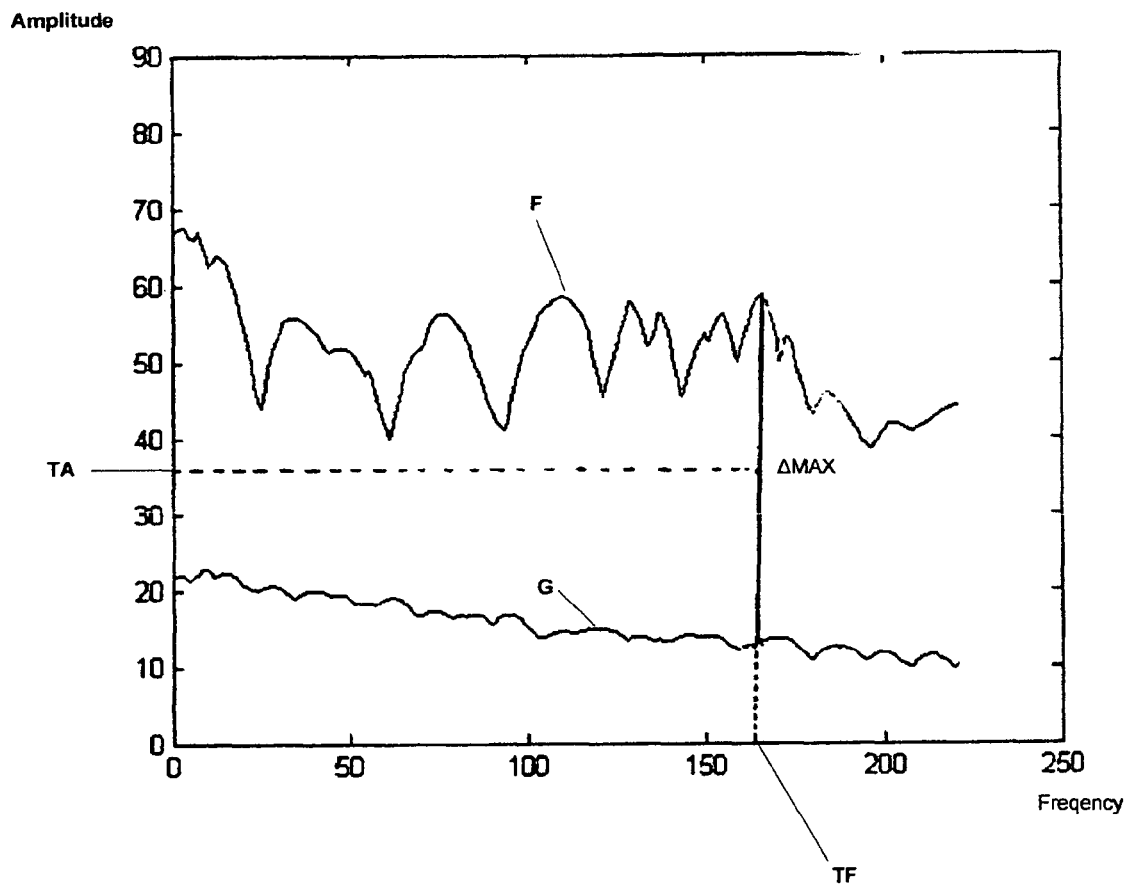
FIG. 14 is a graph showing the location of threshold values derived during the calibration process.

The calibration process then determines thresholds that are to be used to determine whether a received acoustic signal results from a cough or speech, FIG. 14. For each frequency at which analysis is carried out, the maximum speech amplitude (over all speech calibration files) G is subtracted from the minimum cough amplitude (over all cough calibration files) F. This generates a difference value for each frequency at which analysis is carried out. The frequency at which the largest difference (ΔMAX) occurs is selected and nominated as the trigger frequency (TF) for the subject. The frequencies at which the second, third, fourth and fifth largest differences occur are selected and nominated as the confirmatory frequencies (CF1, CF2, CF3, CF4) for the subject.

The midpoint between the cough point and the speech point at the trigger frequency defines the trigger amplitude (TA). Subsequently, if during the monitoring period the amplitude of a noise at the trigger frequency (TF) exceeds this trigger amplitude (TA), it will be designated a potential cough, and if the amplitude at the trigger frequency (TF), is less than the trigger amplitude (TA) it will be designated a non-cough event.

Similarly, the midpoint between the cough points and the speech points at the confirmatory frequencies (CF1, CF2, CF3, CF4) define four confirmatory amplitudes (CA1, CA2, CA3, CA4). The confirmatory amplitudes (CA1, CA2, CA3, CA4) are used to help assess whether a sound was a cough or speech.

Referring back to FIG. 1, the description presented above, has been concerned with calibration carried out at step S1. Operation of step S2 is now described.

Having completed calibration as described above, the sensor 1 remains affixed to the subject in the manner described above for a predetermined time period. The sensor interface 4 also accompanies the subject during this time, and can conveniently be provided with a belt clip or the like to ease transportation. The sensor interface 4 makes a continuous recording of data obtained by the sensor 1 in the non-volatile storage 19, under control of the processor 18. In addition to the piezoelectric sensor described above, an air-coupled microphone is also positioned on the lapel of the patient in preferred embodiments of the invention. The lapel microphone records all noises that are made during the period the subject is wearing the sensor. The microphone recording can be used to validate the results of the piezoelectric sensor manually or automatically and can be used as a diagnostic tool e.g. for detecting sputum or wheeze in a cough.

Data obtained by the sensor interface 4 is then provided to the workstation 3 for analysis. This data provision can be by means of direct a wired connection over, for example a serial interface or memory card transfer. However in alternative embodiments of the invention data is transferred from the sensor interface 4 to the workstation 3 over a computer network. For example, a user may connect the sensor interface 4 to a modem and telephone line to allow data to be transmitted to the workstation 3. Alternatively, the sensor interface 4 may include telecommunications means allowing data to be passed to the workstation 3 in real time.

Data received at the workstation 3 is processed at step S3 of FIG. 1. This processing involves identification of significant vibrations as described above. Each significant vibration is filtered as described above. Having carried out this filtering, an amplitude for each frequency value of interest within a particular significant vibration is obtained. This data is then analysed to determine the number of coughs made by the subject in the period. The analysis is divided into two stages. A first stage is shown in the flowchart of FIG. 15.

Figure 15:
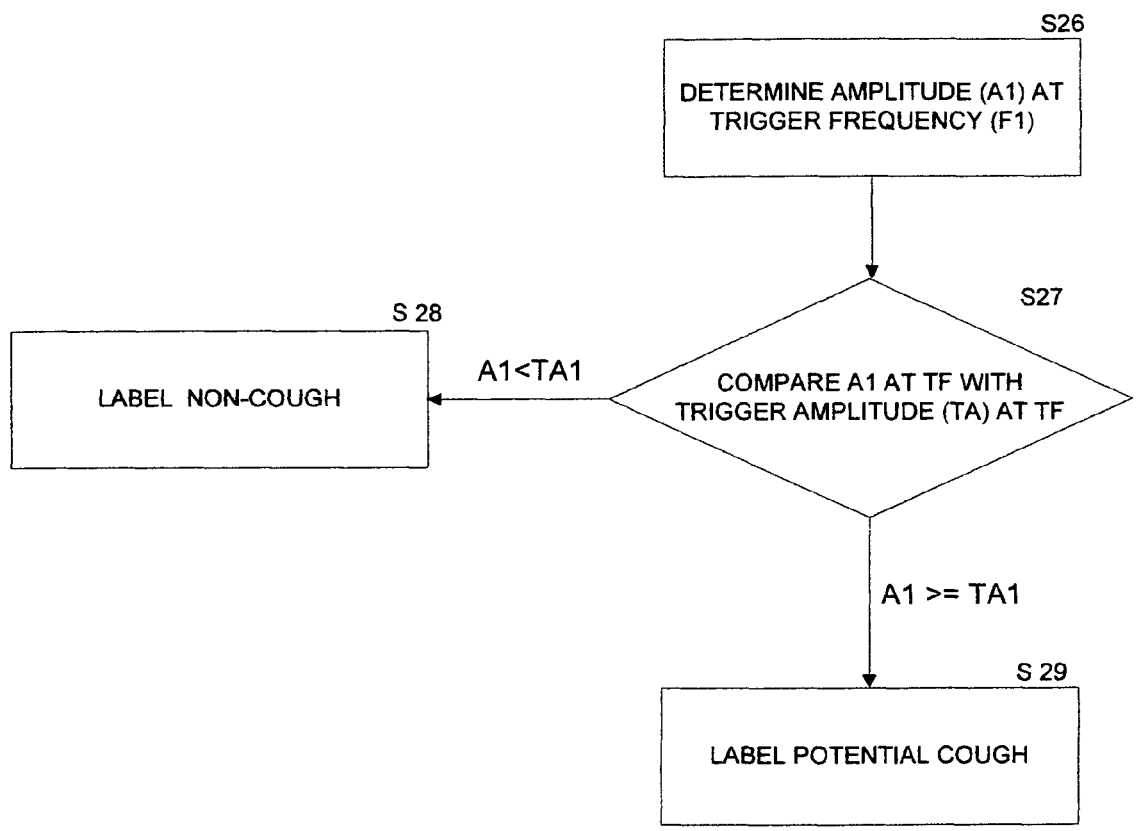
FIG. 15 is a flowchart showing the distinguishing step of FIG. 1 in further detail.

Referring to FIG. 15, at step S26, the amplitude of each significant vibration at the trigger frequency (TF) is determined. The determined amplitude is compared with the trigger amplitude (step S27). If the determined amplitude does not exceed the trigger amplitude (TA), the recording is rejected and labelled a non-cough at step S28. If that amplitude exceeds the trigger amplitude (TA), the recording of the associated vibration is labelled a potential cough at step S29 and output to a second stage of analysis.

In the second stage of analysis, the potential cough is analysed at each of the confirmatory frequencies (CF). The amplitude of the vibrations at these frequencies is compared to the corresponding confirmatory amplitudes (CA). If the amplitudes of vibrations caused by the processed signal, at the confirmatory frequencies, are larger than:

1. all four confirmatory amplitudes at the respective confirmatory frequencies, then the noise is determined to be a cough and appropriate data is recorded;
2. only three confirmatory amplitudes at the respective confirmatory frequencies, then the noise is recorded as a potential cough implying a manual inspection using data obtained using the lapel microphone to be necessary; and
3. only two, one or none of the confirmatory amplitudes at the respective confirmatory frequencies, then the noise is recorded as a non-cough.

Although preferred embodiments of the present invention have been described in detail, it will be appreciated that other implementations are possible without departing from the spirit and scope of the present invention, as set out in the appended claims.

The invention claimed is:

1. A calibration method for calibrating an apparatus comprising a process to differentiate acoustic signals attributable to cough from other acoustic signals, the method comprising:
   receiving, by the processor, first data representing a first acoustic signal representing at least one cough;
   receiving, by the processor, second data representing a second acoustic signal representing an acoustic event other than cough; and
   processing, by the processor, said first and second data to generate configuration data for said apparatus, said configuration data defining at least one rule which when applied differentiates acoustic signals attributable to cough from other acoustic signals, wherein said rule is defined by one or more selected frequencies each having an associated amplitude and the one or more selected frequencies are each selected from a plurality of predetermined frequencies such that the amplitude of said first and second acoustic signals at said selected frequencies has a difference greater than the difference between the amplitude of said first and second acoustic signals at all others of said predetermined frequencies.

2. The method according to claim 1, wherein the amplitude associated with each selected frequency is defined to be centrally placed between the amplitude of said first acoustic signal, and said amplitude of said second acoustic signal at the respective selected frequency.

3. The method according to claim 1, further comprising:
   filtering at least one of said first and second data to remove vibrations below a predetermined amplitude.

4. The method according to claim 1, further comprising:
   filtering the received data representing at least one cough by removing data that represents vibrations with a frequency that exceeds an upper cough cut off frequency.

5. The method according to claim 1, further comprising:
   filtering at least one of said first and second data to remove frequency components above a predetermined frequency threshold.

6. The method according to claim 1, further comprising:
   filtering at least one of said first and second data to remove frequency components below a predetermined frequency threshold.

7. A device storing processor executable program instructions to perform a method of calibrating an apparatus to differentiate acoustic signals attributable to cough from other acoustic signals according to claim 1.

8. A computer apparatus comprising:
   a program memory containing processor readable instructions; and
   a processor for reading and executing the instructions contained in the program memory;
   wherein said processor readable instructions comprise instructions controlling the processor to carry out the method of claim 1.

9. A calibration method for calibrating an apparatus comprising a processor to differentiate acoustic signals attributable to cough from other acoustic signals, the method comprising:
   receiving, by the processor, first data representing a first acoustic signal representing at least one cough;
   receiving, by the processor, second data representing a second acoustic signal representing an acoustic event other than cough; and
   processing, by the processor, said first data and second data together to generate configuration data for said apparatus, said configuration data defining at least one single rule which when applied to a received acoustic signal generates data indicating whether said received acoustic signal is attributable to cough or is attributable to an acoustic event other than cough, wherein the at least one rule is defined by at least one selected frequency and a respective threshold amplitude associated with each of the one or more selected frequencies, and the at least one rule is configured to be applied to said received acoustic signal by a comparison of the amplitude of the at least one selected frequency component of the received signal with the threshold amplitude associated with that frequency.

10. A calibration method according to claim 9, wherein the second acoustic signal represents speech sounds emanating from said subject.

* * * * *